(12) United States Patent
Jeon et al.

(10) Patent No.: US 8,614,084 B2
(45) Date of Patent: Dec. 24, 2013

(54) **MICROBIAL STRAIN *ALTEROMONAS* SP. SN2 FOR DEGRADING POLYCYCLIC AROMATIC HYDROCARBON**

(75) Inventors: Che Ok Jeon, Seoul (KR); Hyun-Mi Jin, Anyang-si (KR); Se Hee Lee, Siheung-si (KR); Jeong Myeong Kim, Seoul (KR); Hyo Jung Lee, Uijeongbu-si (KR)

(73) Assignee: Chung-Ang University Industry-Academy Cooperation Foundation, Seoul (KR)

( * ) Notice: Subject to any disclaimer, the term of this patent is extended or adjusted under 35 U.S.C. 154(b) by 334 days.

(21) Appl. No.: 12/802,111

(22) Filed: May 28, 2010

(65) Prior Publication Data

US 2011/0129902 A1 Jun. 2, 2011

(51) Int. Cl.
*C12N 1/20* (2006.01)

(52) U.S. Cl.
USPC .................................. 435/252.1; 435/262.5

(58) Field of Classification Search
None
See application file for complete search history.

(56) References Cited

U.S. PATENT DOCUMENTS 5,888,396 A * 3/1999 Perriello ...................... 210/611

OTHER PUBLICATIONS

Hedlund, B.P., Conference Proceedings, "American Society for Microbiology, 96th General Meeting, New Orleans, May 1996", Abstract.*

Zaidi et al. "Factors Affecting Microbial Degradation of Polycyclic Aromatic Hydrocarbons Phenanthrene in the Caribbean Coast Water" Marine Pollution Bulletin vol. 38, No. 8. pp. 737-742, 1999.*
Jin et al., "Isolation of New Naphthalene Degrading Bacteria from Oil-Contaminated Marine Sediment and Their Naphthalene Degradation Ability," MSK's 50th Anniversary International Symposium on Microbiology 2009, May 28-30, 2009, The Microbiological Society of Korea (MSK).
Cui et al., "Biodiversity of Polycyclic Aromatic Hydrocarbon-Degrading Bacteria from Deep Sea Sediments of the Middle Atlantic Ridge," Environ. Microbiol. 10(8):2138-2149, 2008.

* cited by examiner

*Primary Examiner* — Blaine Lankford, Jr.
*Assistant Examiner* — Lauren K Van Buren
(74) *Attorney, Agent, or Firm* — Clark & Elbing LLP

(57) ABSTRACT

The present invention relates to a novel microbial strain, *Alteromonas* sp. SN2 (KCTC11700BP) having an activity for degrading polycyclic aromatic hydrocarbon (PAH), a bioremediation process of polycyclic aromatic hydrocarbon (PAH) contaminants, comprising contacting a microbial strain *Alteromonas* sp. with PAH, and a composition for purifying polycyclic aromatic hydrocarbon (PAH) contaminants, comprising a microbial strain *Alteromonas* sp. It is advantageous that the present invention may be suitably utilized in treatment or remediation of oil contaminants, particularly naphthalene soil contaminants without production of a secondary contaminant source. As the strain and bioremediation process of this invention could be industrially utilized through low-cost and environment-friendly process, the present technology also may be carried out much more economically and efficiently than conventional technologies such as thermal technology, solidification technology, and vapor extraction technology.

3 Claims, 6 Drawing Sheets
(2 of 6 Drawing Sheet(s) Filed in Color)

SEQUENCE LISTING

<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
ctggcwwtty ctcacycat                                                  19

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tcsgcrggtg ycttccagtt g                                               21

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gacgtsaacw ssgactggac                                                 20

<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
aacgagctsc gscagac                                                    17

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tcsgcctcca tgtasagcca                                                 20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ttcgagctgg aatgtgagc                                                  19

<210> SEQ ID NO 7
<211> LENGTH: 20
<212> TYPE: DNA

```
<213> ORGANISM: Artificial Sequence
<220> FEATURE:
<223> OTHER INFORMATION: primer

<400> SEQUENCE: 7
aataaccggc gattccaaac                                              20

<210> SEQ ID NO 8
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 8
gtymgncaym gngg                                                    14

<210> SEQ ID NO 9
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 9
ccanccrtgr tanswrca                                                18
```

MICROBIAL STRAIN ALTEROMONAS SP. SN2 FOR DEGRADING POLYCYCLIC AROMATIC HYDROCARBON

CROSS REFERENCE TO RELATED APPLICATIONS

This application claims priority from foreign patent application 10-2009-0116224, filed Nov. 27, 2009, in the Republic of Korea.

BACKGROUND OF THE INVENTION

1. Field of the Invention

The present invention relates to a marine bacterium, *Alteromonas* sp. SN2 (KCTC11700BP) having an activity for degrading polycyclic aromatic hydrocarbon (PAH), a bioremediation process of PAH contaminants using the same, and a composition for purifying PAH contaminants using the same.

2. Description of the Related Art

Naphthalene flowed into wastewater during bioremediation processes of petroleum or coke because it was highly contained in oil or coal tar. Likewise, wastewater containing naphthalene may be a crucial factor causing difficulty in manipulation of wastewater treatment system, for example including inhibition of microorganism growth and delay of reaction time during activated sludge processes. Conventionally, solvent extraction method has been utilized in removal of naphthalene contained in the wastewater. However, solvent extraction method has severe drawbacks such as low economic efficiency and complicated processes in the senses that chemicals of organic components involved in wastewater are extracted with solvent, followed by combustion or incineration of extracted solvents.

According to the principles of treatment technologies, bioremediation process of contaminated soil is divided into: (a) thermal technology degrading toxic materials by incineration or thermal-decomposition through exposing soil to higher temperature; (b) stabilization and solidification technology preventing contaminant transport by formation of solid materials; (c) soil vapor extraction technology extracting and treating polluted air through pore of contaminated soil; (d) physical and chemical extraction technology in which a heavy metal is treated with water, acid, organic solvent, etc.; and (e) microbial treatment technology promoting biodegradation of organic chemicals by activating soil bacteria.

The treatment process such as thermal technology, solidification technology and vapor extraction technology has the following problems: (a) secondary contaminations such as incomplete incineration or residual solvents, and environmental disturbance, and (b) higher treatment cost.

Meanwhile, bioremediation is a process in which a toxic material is converted into a material having low toxicity using a microorganism or its metabolite. This technology utilizes a process in which contaminants are converted into non-toxic carbon dioxide by microorganism using them as carbon and energy source. This technology is based on carbon cycle, and carried out whereby carbon is repeatedly cycled through redox reactions between inorganic and organic material (Roling, W. F. M. et al. The microbiology of hydrocarbon degradation in subsurface petroleum reservoirs: Perspectives and prospects. *Res. Microbiol.* 154: 321-328 (2003)).

In this context, economics and efficiency of bioremediation have been already demonstrated in numerous case studies and practical application studies in the senses that bioremediation not only allows much more lower secondary contaminations, but also most economical processes up to now due to natural attenuation's ability (Margesin R, Schinner F. Bioremediation (Natural Attenuation and Biostimulation) of Diesel Oil Contaminated Soil in an Alpine Glacier Skiing Area. *Applied and Environmental Microbiology* 67: 3127 (2001)).

As supply source of microbes, there are the following methods: (a) bio-stimulation method using indigenous microorganisms propagating in a contaminated region; and (b) bio-augmentation method supplying foreign microorganisms having an activity for degrading a specific contaminant, which are massively cultured in the laboratory. Particularly, the latter method has shortcomings such as: (a) high probability that foreign microorganism injected fails to be predominant species due to defeat in survival competence with indigenous microorganisms; and (b) high possibility that unexpected environmental disturbance is caused by metabolites of foreign microorganism.

Example of the former method is as follows: (a) a method for removing contaminants by growing and proliferating indigenous microorganism without injection of foreign microbe to a polluted region; and (b) a method that indigenous microorganism isolated are massively cultured in the laboratory and re-injected into a contaminated region. The former has a demerit that total restoration period in a polluted region is prolonged for a long time as lag time is excessively required in an early restoration period until indigenous microorganisms reach at above certain individual number.

Therefore, the methods to utilize microorganisms cultured massively in the laboratory have been applied to overcome defects as described above, and there has been urgently demanded the necessity of novel microbial strains and processes for biologically purifying soil, fresh water or seawater contaminated with any type of oil (particularly, naphthalene).

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventors have done intensive studies to develop a method for degrading PAH compounds such as naphthalene and phenanthrene, in which secondary contaminants are minimally produced using natural attenuation's ability. As results, we have discovered that a strain, *Alteromonas* sp. SN2 (KCTC11700BP), isolated from a contaminated tidal flat with oil spills is able to degrade PAH compounds such as phenanthrene and naphthalene in more efficient manner, and polluted marine environments may be biologically cleaned through bioremediation using the same.

Accordingly, it is an object of this invention to provide a microbial strain, *Alteromonas* sp. SN2 (KCTC11700BP) having an activity for degrading polycyclic aromatic hydrocarbon (PAH).

It is another object of this invention to provide bioremediation processes of polycyclic aromatic hydrocarbon (PAH) contaminants, especially in marine environments, comprising a microbial strain *Alteromonas* sp.

It is still another object to this invention to provide a composition for purifying polycyclic aromatic hydrocarbon (PAH) contaminants, comprising a microbial strain *Alteromonas* sp.

Advantages of the present invention will become apparent from the following detailed description together with the appended claims and drawings.

In one aspect of this invention, there is provided a novel microbial strain, *Alteromonas* sp. SN2 (KCTC11700BP) having an activity for degrading polycyclic aromatic hydrocarbon (PAH).

The present inventors have done intensive studies to develop a method for degrading PAH compounds, in which secondary contaminants are minimally produced using natural attenuation's ability. As results, we have discovered that a strain isolated from a contaminated tidal flat with oil spills is able to degrade PAH compounds such as Naphthalene and phenanthrene in more efficient manner and polluted soil and seawater may be biologically purified through bioremediation using the same.

The term "polycyclic aromatic hydrocarbons (PAHs)" used herein refers to a chemical compound consisting of fused aromatic rings having no hetero atom and delivering a substituted group[13]. PAHs are chemical compounds which are generated in oil, coal and tar products, and, produced as by-products during fuel (fossil fuel or biomass) combustion. Of them, a part of chemicals are clearly described as chemicals inducing carcinogenesis, mutation and deformed child.

According to this invention, the nucleotide sequence of 16S rRNA gene in selected microorganism was determined using phylogenic analysis, and identified as a novel microorganism belonging to *Alteromonas* sp. This microorganism named as "*Alteromonas* sp. SN2", was deposited on May 14, 2010 in International Depository Authority of Korean Collection for Type Cultures (KCTC, Address: "Korean Research Institute of Biosciences and Biotechnology (KRIBB), 111 Gwahangno, Yuseong-gu, Daejeon, 305-806 Republic of Korea") under the accession number of KCTC11700BP, which is recognized by the World Intellectual Property Organization (WIPO) under the Budapest Treaty on the international recognition of the deposit of microorganisms for the purpose of patent procedure.

According to previous reports, no *Alteromonas* sp. has been known to have activity for degrading any PAH compound and to express naphthalene-1,2-dioxygenase gene (STEFANIE Van T et al, *Alteromonas stellipolaris* sp. nov., a novel, budding, prosthecate bacterium from Antarctic seas, and emended description of the genus *Alteromonas*, *Intl Syst Evol Microbiol*; 54: 1157-1163 (2004)).

According to one embodiment, strain SN2 as a novel microorganism of this invention is the first *Alteromonas* microbe having an excellent activity for degrading naphthalene among PAHs. Given that strain SN2 has an activity for degrading PAHs, it could be appreciated that the microbe of the present invention is a novel strain very different to conventional *Alteromonas* sp.

According to a preferable embodiment, the strain *Alteromonas* sp. SN2 of the present invention has an activity for degrading PAH compounds; naphthalene, anthracene, chrysene, benzo[a]pyrene, coronene, corannulene, naphthacene, pentacene, phenanthrene, pyrene, triphenylene or ovalene, more preferably naphthalene, anthracene, chrysene or benzo[a]pyrene, and most preferably naphthalene and phenanthrene.

The strain *Alteromonas* sp. SN2 (KCTC11700BP) of the present invention expresses naphthalene-1,2-dioxygenase catalyzing PAH compound degradation.

Illustrative example of chemical equation for naphthalene and phenanthrene degradation (ring compound cleavage pathway) is as follows:

naphthalene+NADH+H⁺+O₂ ↔ (1R,2S)-1,2-dihydronaphthalene-1,2-diol+NAD⁺

According to a preferable embodiment, the present invention provides a novel *Alteromonas* sp. SN2 strain (KCTC11700BP) having an activity for biodegrading PAH compounds through expression of naphthalene-1,2-dioxygenase.

According to this invention, the novel *Alteromonas* sp. SN2 strain (KCTC11700BP) was isolated from tidal flat near Ulhang-ri in Taean-Gun, Chungcheongnam-do, Republic of Korea contaminated with oil spill, and was identified as a strain having an excellent activity for degrading a polycyclic aromatic ring compound, particularly naphthalene. Therefore, the strain may be provided for biologically purifying soil contaminated with polycyclic aromatic ring compounds.

According to a preferable embodiment, the microorganism of this invention is isolated from tidal flat.

In another aspect of this invention, there is provided a bioremediation process of polycyclic aromatic hydrocarbon (PAH) contaminants, comprising contacting a microbial strain *Alteromonas* sp. with PAH contaminants.

The bioremediation process of the present invention utilizes the *Alteromonas* sp. of this invention having a remarkable activity for degrading PAHs. The method of the present invention expresses a bioremediation process of PAH contaminants. Alternatively, the method may express a restoration or bioremediation process of PAH contaminant sediment.

According to a preferable embodiment, the PAH contaminants include naphthalene, anthracene, chrysene, benzo[a]pyrene, coronene, corannulene, naphthacene, pentacene, phenanthrene, pyrene, triphenylene or ovalene contaminants, more preferably naphthalene, anthracene, chrysene or benzo[a]pyrene contaminants, and most preferably naphthalene contaminants.

The *Alteromonas* sp. of this invention includes a naphthalene-1,2-dioxygenase gene or a naphthalene-degrading factor.

According to a preferable embodiment, the *Alteromonas* sp. of this invention is the *Alteromonas* sp. SN2 strain (KCTC11700BP), and most preferably the *Alteromonas* sp. SN2 strain (KCTC11700BP) having an activity for biodegrading naphthalene through expression of naphthalene-1,2-dioxygenase.

According to a preferable embodiment, the strain used in the present invention is isolated from tidal flat.

The bioremediation process of the present invention may be varied depending on kinds of contaminants.

According to a preferable embodiment, PAH contaminants capable of being treated with the process of the present invention include soil, fresh water or seawater polluted with PAHs, and most preferably soil polluted with PAHs.

Where contaminants to be treated in the present invention are soil, practical example of the present process is as follows:

The method of this invention for restoring contaminated soils may be determined depending on excavation of soil, for example including in-situ bioremediation, composting, and biological bioreactor process.

(a) In-Situ Bioremediation Process:

For in-situ bioremediation of soil and groundwater, oxygen is injected for accelerating specific microorganism activity on standard environment, and if necessary, treated water is injected after nutrients and other additives were mixed with inflow water, and inhaled again. Water permeability is a very important hallmark for biological treatment in in-situ state, and the Kf-value of 10-5 m/s is generally considered as a minimal water permeability factor for successful treatment (Watanabe, K. Microorganisms relevant to bioremediation. *Curr. Opin. Biotechnol.* 12: 237-241 (2001)).

(b) Composting Process:

To promote biodegradation rate of contaminants by microbes, excavated soil contaminated was stacked as a compost pile and turned upside down periodically for supplying oxygen and water. During this process, toxic materials capable of being biodegraded by microbes are converted into stable non-toxic by-products at 50-55° C. (Mar J A. Bioremediation by composting of heavy oil refinery sludge in semiarid conditions. *Biodegradation.* 17(3): 251-261 (2006)). While the compost pile is stacked, soil is mixed with an organic material such as bulking agent or wood carving, sawdust and vegetable waste to increase void ratio within contaminated soil, and then the compost pile with height of 0.9-1.8 m is arranged in a row.

(c) Bioreactor Process:

Excavated soil contaminated are mixed with water and suitable additive, and then injected into bioreactor, followed by shaking. Consequently, microorganisms are activated to promote naphthalene degradation. This method has characteristics of higher efficiency on contamination treatment by successively injecting microorganism, oxygen source and nutrient solution into bioreactor.

The method of the present invention may be not particularly limited to the processes as described above, and carried out using various processes commonly known in the art.

Since the present method comprises the *Alteromonas* sp. SN2 strain (KCTC11700BP) of this invention described above, the common descriptions between them are omitted in order to avoid undue redundancy leading to the complexity of this specification.

In still another aspect of this invention, there is provided a composition for clearing polycyclic aromatic hydrocarbon (PAH) contaminants, comprising a microbial strain *Alteromonas* sp.

The composition may include nitrogen and phosphorous insufficient in contaminated soil, oxygen-generating materials such as hydrogen peroxide, surfactants for accelerating surface contact between contaminants and microorganisms, and enzymes suitably activating several steps for biochemically degrading contaminants. Likewise, the reason that additives as well as microorganisms are necessary is because growth condition of microorganism is very poor in soil contaminated with PAHs of high concentration. However, *Alteromonas* sp. SN2 can grow and degrade PAH compounds very fast in almost all kinds of nutrient media if the media contain 0.5%~5% (w/v) NaCl.

In addition to the *Alteromonas* sp., the composition of this invention may be not limited to components as described above and include various components known to those ordinarily skilled in the art to promote activation of microorganisms and degradation of contaminants.

According to a preferable embodiment, PAH contaminants capable of degrading composition include naphthalene, anthracene, chrysene, benzo[a]pyrene, coronene, corannulene, naphthacene, pentacene, phenanthrene, pyrene, triphenylene or ovalene contaminants, more preferably naphthalene, anthracene, chrysene or benzo[a]pyrene contaminants, and most preferably naphthalene contaminants.

According to a preferable embodiment, the *Alteromonas* sp. in the composition of this invention is the *Alteromonas* sp. SN2 strain (KCTC11700BP), and most preferably the *Alteromonas* sp. SN2 strain (KCTC11700BP) having an activity for biodegrading naphthalene and phenanthrene through expression of naphthalene-1,2-dioxygenase.

According to a preferable embodiment, the strain contained in the composition of the present invention is isolated from tidal flat.

According to a preferable embodiment, PAH contaminants capable of being treated with the composition of the present invention include soil, seawater contaminated with PAHs, and most preferably soil contaminated with PAHs.

Since the present composition comprises the *Alteromonas* sp. SN2 strain (KCTC11700BP) of this invention described above, the common descriptions between them are omitted in order to avoid undue redundancy leading to the complexity of this specification.

The features and advantages of this invention are summarized as follows:

(a) The present invention provides a microbial strain, *Alteromonas* sp. SN2 (KCTC11700BP) having an activity for degrading naphthalene and phenathrene, and a process and a composition for degrading naphthalene and phenathrene contaminants using the same.

(b) it is advantageous that the present invention may be suitably utilized in restoration or bioremediation of oil contaminants, particularly naphthalene soil contaminants without production of a secondary contaminant source.

(c) The present invention may be advantageous for applying to various contaminated environments because of the high growth rate and high settlement of *Alteromonas* sp. SN2 various contaminated environments.

(d) The present invention may apply to various contaminated murine environments such as sea tidal flats and seawater without addition of salts.

(f) As the strain and bioremediation process of this invention could be industrially utilized through low-cost and environment-friendly process, the present technology also may be carried out much more economically and efficiently than conventional technologies such as thermal technology, solidification technology, and vapor extraction technology.

BRIEF DESCRIPTION OF THE DRAWINGS

The file of this patent or application publication contains at least one drawing executed in color. Copies of this patent or application publication with color drawing(s) will be provided by the Office upon request and payment of the necessary fee.

EXPERIMENTAL MATERIALS AND METHODS

1. Soil Sampling

Soil samples were harvested from tidal flat near Ulhang-ri in Taean-Gun contaminated from Hebei Spirit oil spill began on December 2007. Sample harvest was performed every month, resulting in eight samples (periods: 28 Dec. 2007-29 Jul. 2008). Soil used in the experiments was the soil 1 month at post-accident, and stored at −80° C. until use after harvest of about 150 ml soil per experiment.

2. Microorganism Enrichment Culture and gDNA (Genomic DNA) Extraction Microorganism Enrichment Culture As enrichment culture media, the present inventors utilized artificial media mixing MSB (basal salts medium, stucker et al., 1996)[11] and ASW (artificial sea water, Kester et al., 1967)[12] at a ratio of 1:1 for providing environment similar to seawater that called M-MSB, and sea water transferred from soil of mud flat in harvest region. Naphthalene was added to each 150 ml medium as single carbon source, and 15 g soil (10% weight of total media) obtained from sample harvest was inoculated into the media. Each samples was subcultured four times in equal media prepared under equal conditions at an interval of two weeks. For subculture, a part of supernatant (10 ml) obtained from previous enrichment culture media was inoculated into fresh media (total enrichment culture period; eight weeks, 25° C., 180 rpm). In addition, the precipitates were harvested by centrifugation (13000×g, 5 min) of the part of sample for microorganism population analysis according to enrichment culture period as indicated.

3. Microorganism Diversity in Naphthalene Environment

After enrichment culture for eight weeks, the supernatant of final samples was collected and then 100 μl supernatants at a dilution rate of $10^{-3}$-$10^{-4}$-fold were spread at marine agar plate media, respectively. The plates were cultured for 2 days, and PCR (polymerase chain reaction) for 16S RNA gene was carried out in single colonies (the strain capable of utilizing carbon source by degrading naphthalene) forming the population. Primers for detecting 16S rRNA gene as an universal primer was used as follows: 1F, 5'-AGA GTT TGA TCM TGG CTC AG-3'; and 13R, 5'-TAC GGY TAC CTT GTT ACG ACT T-3'. PCR condition was as follows: 32 cycles consisting of denaturation at 94° C. for 45 sec, annealing at 56° C. for 45 sec, and extension at 72° C. for 45 sec; and further incubating at 72° C. for 10 min (PCR Master Mix: 10×PCR buffer 2.5 μl, 100 mM dNTPs 0.5 μl, dDW: 18.75 μl, 10 pmol PCR primer 1 μl, Taq polymerase 0.125 μl and template 1 μl).

4. ARDRA (Amplified rDNA Restriction Analysis)

As results, ARDRA was performed using 16S rRNA gene PCR products (amplicons) of each strain. PCR products were restricted with HhaI (NEB, UK) and HeaIII restriction enzymes for 6 hrs, and electrophoresized on 2% metaphore agar gel (BioWhittaker, USA) in 1% TBE buffer for 70 min, followed by RFLP (restriction fragment length polymorphism). After the analysis of fragment patterns and purification, 16S rRNA genes were sequenced.

5. Naphthalene and Phenanthrene Degradation Test

A portion of single strains selected was inoculated into 5 ml marine broth (Difco) and cultured for 48 hrs. Single strain was sufficiently cultured at serum bottle supplemented with total 10 ml of 1×M-MSB media and each PAH compound of about 30 ppm concentration, and then $1.0 \times 10^7$ cells of strain SN2 was inoculated into serum bottle, and the serum bottle was completely sealed using silicon cap and aluminium cap. The strain was cultured at 180 rpm for 14 days at 25° C. as triplicate.

6. Gas Chromatography Analysis

After degradation test for 2 weeks, serum bottles were opened and added with 5 ml ethylether (Fisher scientifics) supplemented with 50 ppm internal standard (1-chloronaphthalene; Sigma-Aldrich). After shaking, only the supernatant in the serum bottle was collected and the amount of residual naphthalene was measured using Gas Chromatography model 6890N (Agilent Technologies Company).

7. Phylogenic Tree of the SN2 Strain

For phylogenic analysis of the SN2 strain, 16S rRNA gene was amplified with F1 and R13 primer, and the nucleotide sequence (1,350 nucleotides) of PCR products was analyzed. And then, the similar type strain of γ-Proteobacteria was researched using NCBI GenBank (http://www.ncbi.nlm.nih.gov/BLAST/), generating phylogeny tree with the SN2 strain. According to homology of nucleotide sequence, genes were aligned using CLUSTAL W software program, and their phylogenic tree was drawn by PHYLIP software (version 3.6, Felsenstein, 2002) using neighbor-joining, NJ, maximum-likelihood (ML) and maximum-parsimony (MP) method.

8. gDNA Extraction gDNA was extracted from the precipitated soil subcultured under the condition at 4° C., and 0.5 g soil of tidal flat using gDNA extraction kit (MPbio medical, Inc., Fast@DNA spin for Soil kit) and bead beater (bead beater; Biospec Products, Bartlesville, USA).

9. DGGE (Denaturing Gradient Gel Electrophoresis) Analysis

DGGE experiments were carried out on 8% acrylamide gel containing urea and formamide at a linear gradient range of 30-60%. For DGGE analysis, gDNA extracted from the precipitates of sample after enrichment culture, PCR products of the SN2 strain amplified with gc338F (5'-CGC CCG CCG CGC GGC GGG CGG GGC GGG GGC ACG GGG GGA CTC CIA CGG GAG GCA GCA G-3') and 758R (5'-CTA CCA GGG TAT CTA ATC C-3') primer, and gDNA of soil contaminated after oil spill were utilized as DNA templates, and then 10 μl PCR products were loaded at Bio-Rad Dcode system (electrophoresis at 70V for 15 hrs at 60° C.), respectively. The gel was stained with 0.5×SYBR Green I (Invitrogen, USA) for 30 min.

10. Detection of Naphthalene-1,2-dioxygenase Gene

The nucleotide sequences of well-known naphthalene-1,2-dioxygenase genes were examined to prepare primer (Table 1). The SN2 strain was PCR-amplified with each primer set.

TABLE 1

| Primer name | Nucleotide sequence (5'→3') | Size (bp) |
|---|---|---|
| NahAc114f | CTGGCWWTTYCTCACYCAT | 480 bp |
| NahAc 595R | TCSGCRGGTGYCTTCCAGTTG | |
| NDO gene F200 | GACGTSAACWSSGACTGGAC | 1500 bp |
| NDO gene F201 | AACGAGCTSCGSCAGAC | 1500 bp |
| NDO gene F202 | TCSGCCTCCATGTASAGCCA | |
| Phn gene P8073 | TTCGAGCTGGAATGTGAGC | 933 bp |
| Phn gene P9047 | AATAACCGGCGATTCCAAAC | |
| Rieske F | GTYMGNCAYMGNGG | 78 bp |
| Rieske R | CCANCCRTGRTANSWRCA | |

11. Confirmation of Naphthalene Degradation Mechanism

To determine naphthalene degradation pathway of the SN2 strain selected, the colorimetric reaction by indole was observed. 100 μl indole (1 mM, Sigma-Aldrich) was spread on M-MSB agar plates. After spreading on agar plates, the SN2 strain was incubated with naphthalene at 25° C. for 2 days, followed by observing colorimetric reaction.

Experimental Results

1. Strain Selection Using PAHs as Carbon Source

To select a strain using naphthalene and phenanthrene as a single carbon source, enrichment culture was carried out. The samples extracted from enrichment culture solution were incubated on marine agar media, and then the colonies forming on agar plates were selected.

2. ARDRA Results

Figure 1:
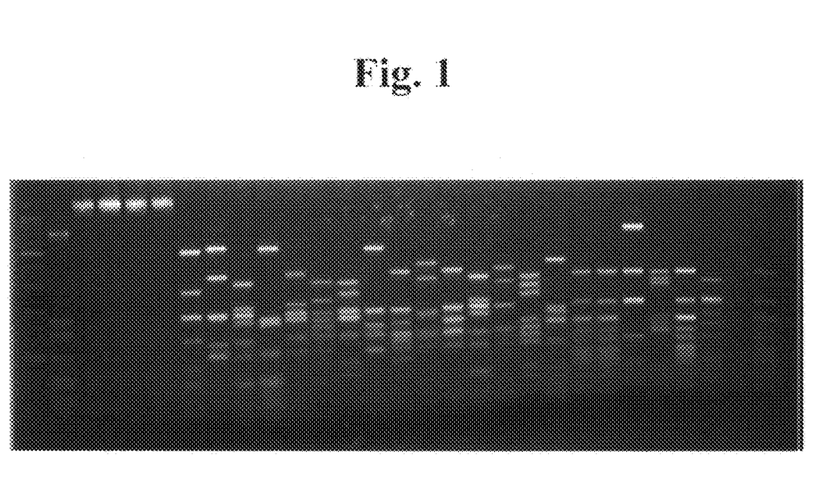
FIG. 1 represents ARDRA (amplified ribosomal DNA restriction analysis) for pattern analysis and grouping of 16S rRNA genes restricted with HhaI and HeaIII. Gel image indicates pattern of microbial population cultured in sea water under naphthalene enrichment.

ARDRA was carried out by PCR using the strains selected. The 16S rRNA PCR products of each strain were restricted with HhaI (NEB, UK) and HeaIII restriction enzymes for 6 hrs, resulting in total eleven ARDRA patterns (FIG. 1). Specific enzyme restriction patterns were observed corresponding to each group, indicating that the strains having the equal pattern completely represent the same kind of microorganism. As determined according to ARDRA pattern, microorganisms were divided and listed.

3. Nucleotide Sequence Analysis of 16S rRNA

According to nucleotide sequence analysis, the list of type strain genetically closest to strains selected using ARDRA was prepared. Among them, a part of type strain of family including microorganisms related to naphthalene degradation such as *Thalassospira* sp. or *Pseudomonas* sp. was often found.

Tablet represents nucleotide sequence analysis of 16S rRNA in microorganism populations extracted from enrichment culture of mudflat samples near Ulhang-ri in Taean-Gun, Chungcheongnam-do, Republic of Korea. In addition, Table 2 was a result using Blast search in NCBI, and represented the closest type strain and its identity.

4. Naphthalene and Phenanthrene Degradation Test

Figure 2:
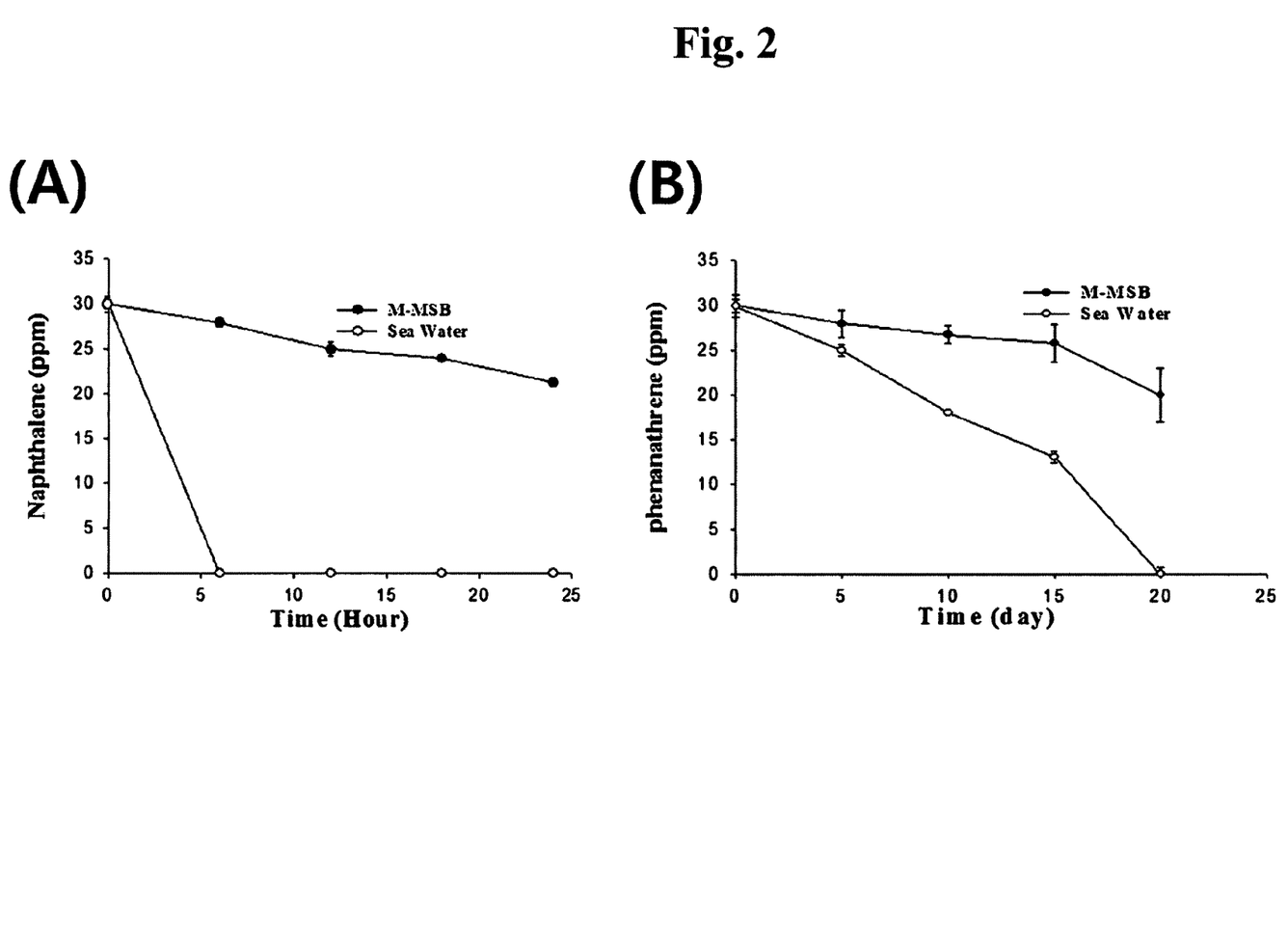
FIG. 2 shows that a microbial strain, SN2 has an activity for degrading naphthalene and phenanthrene. The horizontal and vertical axis indicates degradation test period and the amount of residual naphthalene in serum bottle, respectively. As a control, the residual amount of PAH compounds in serum bottle without inoculation of SN2 were measured under the same media and culture conditions Panel (A) and (B) are typical examples of naphthalene and phenanthrene concentration in the biodegradation experiments, respectively.

According to gas chromatography analysis after biodegradation test were carried out in serum bottle for 14 days using total eleven kinds of strains found in enrichment culture and ARDRA, it was demonstrated that only SN2 strain has a significant activity for degrading naphthalene and phenanthrene in serum bottle supplying each PAH compound as a carbon source. It could be appreciated that the amount of residual naphthalene in the SN2 strain 14 days at post-inoculation was reduced to almost zero compared to that in control without inoculation of strains (FIG. 2). Based on analysis of naphthalene degradation for 14 days, the SN2 strain had a remarkable activity capable of degrading PAHs in serum bottle within 2 days (Table. 2 and FIG. 2).

TABLE 2

| Strain name | Closest strain | Identity | Results of Degradation Test* |
|---|---|---|---|
| Isolated from M-MSB enrichment system | | | |
| AN1 | *Galbibacter mesophilus* Mok-17$^T$ | 687/750 (91%) | − |
| AN2 | *Pseudomonas* sp. | 699/700 (99%) | − |
| AN3 | *Microbacterium maritypicum* DSM 12512$^T$ | 691/693 (99%) | − |
| AN4 | *Serratia odorifera* DSM 4582$^T$ | 644/701 (91%) | − |
| AN6 | *Microbacterium aerolatum* V-73$^T$ | 689/693 (99%) | − |
| AN7 | *Microbacterium maritypicum* DSM 12512$^T$ | 698/700 (99%) | − |
| AN8 | *Pseudoalteromonas nigrifaciens* NCIMB 8614$^T$ | 697/700 (99%) | − |
| AN9 | *Marinobacterium litorale* IMCC1877$^T$ | 683/705 (96%) | − |
| Isolated from seawater enrichment system | | | |
| SN1 | *Thalassospira lucentensis* DSM 14000$^T$ | 519/525 (98%) | − |
| SN2 | *Alteromonas stellipolaris* LMG 21861$^T$ | 526/531 (99%) | +++ |
| SN3 | *Thalassospira xiamenensis* M-5$^T$ | 530/534 (99%) | − |

*Symbols: +, positive; −, negative.

5. DGGE Analysis of 16S rRNA Fragment

Figure 3:
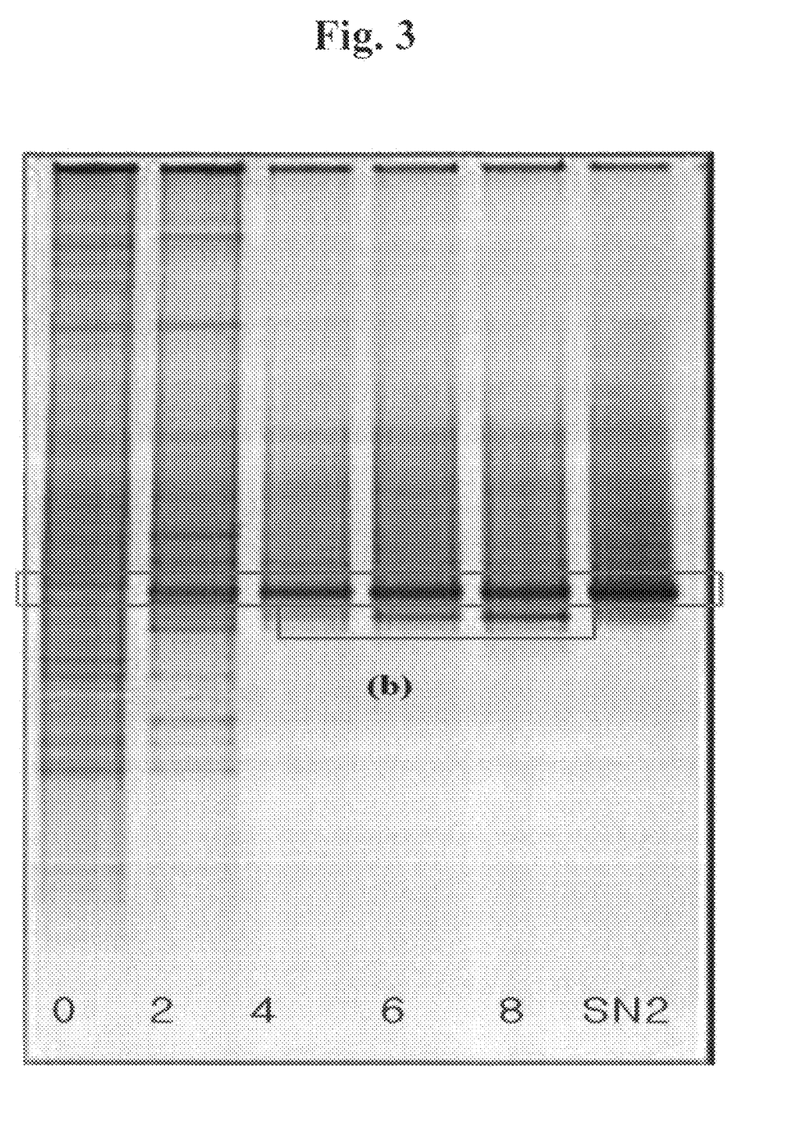
FIG. 3 shows DGGE (denaturing gradient gel electrophoresis) analysis of 16S gene.

In DGGE using GC388F and 758 primers, numerous bands in the precipitates of sample were detected at the same position on the gel as shown in the SN2-type strain (FIG. 3). It was well-known that the density of population could be determined depending on band intensity. The band intensity of the SN2-type strain was gradually increased up to 8-week in a time-dependent manner, whereas other bands detected at a different position represented various patterns, e.g., they exhibited a tendency to be decreased or showed newly bands between six and eight weeks. And, the bands on DGGE gel between six and eight weeks were extracted, and then their nucleotide sequences were analyzed. As results, it was demonstrated that the strain belongs to the SN1-type strain, and shows a similarity of 98% in 16S rRNA gene to *Thalassospira*

*lucentensis* DSM 14000$^T$ strain. *Thalassospira* sp. has been known to contain PAH (polycyclic aromatic hydrocarbon)-degrading microorganisms. However, the SN1-type strain isolated from tidal flat in Taean-Gun had no activity for degrading naphthalene.

6. Phylogenic Tree of SN2-Type Strain

Figure 4:
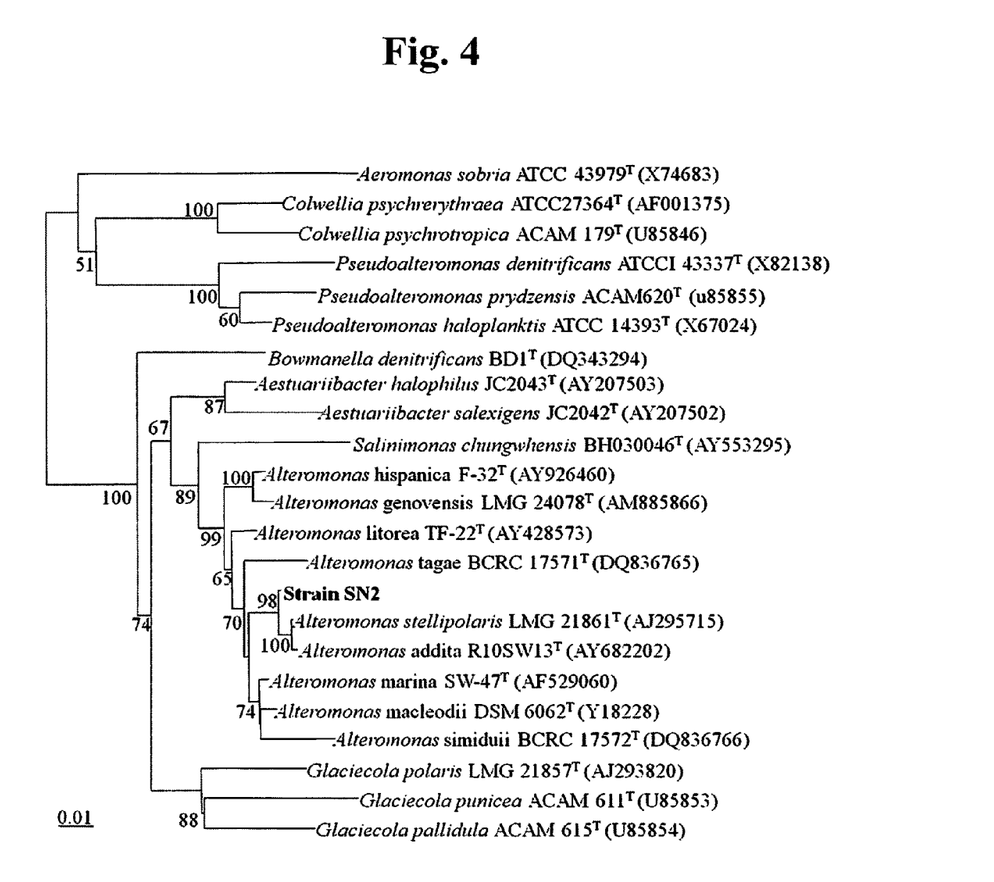
FIG. 4 is a phylogenic tree of the strain SN2

There was provided a phylogenic tree comparing 16S rRNA gene of the SN2 strain with that of various similar type strain of γ-Proteobacteria (FIG. 4). Boot strip value was repeated 1000-times. As a result, the branch representing the consistency of not less than 50% was indicated as a numeric value. The type strain of γ-Proteobacteria related to the SN2 strain was described as GenBank accession number. Consequently, the nucleotide sequence of *Alteromonas stellipolaris* LMG 21861$^T$ (AJ295715) and *Alteromonas addita* R10SW13$^T$ (AY682202) showed a similarity of 98% to that of the SN2 strain. In addition, several strains having a similarity to the SN2 strain were shown in the tree. Accordingly, it could be supposed that the SN2 strain belongs to the genus *Alteromonas*.

Taken together, the SN2 strain having a remarkable activity for degrading naphthalene as a carbon source was named as *Alteromonas* sp. SN2. The SN2 strain had been deposited on Nov. 5, 2009 in Domestic Depository Authority, the RDA (rural development administration)-Genebank information center, Republic of Korea and was given accession number KACC 91504. According to Butapest treaty on the International Recognition of the Deposit of Microorganisms for the Purposes of Patent Procedure, the SN2 strain has been converted to International Deposit on May 14, 2010 in International Depository Authority, the Korean Collection for Type Cultures (KCTC, Address: Korean Research Institute of Biosciences and Biotechnology (KRIBB), 111 Gwahangno, Yuseong-gu, Daejeon, 305-806 Republic of Korea), and was given accession number KCTC11700BP.

7. Detection of Dioxygenase

Figure 5:
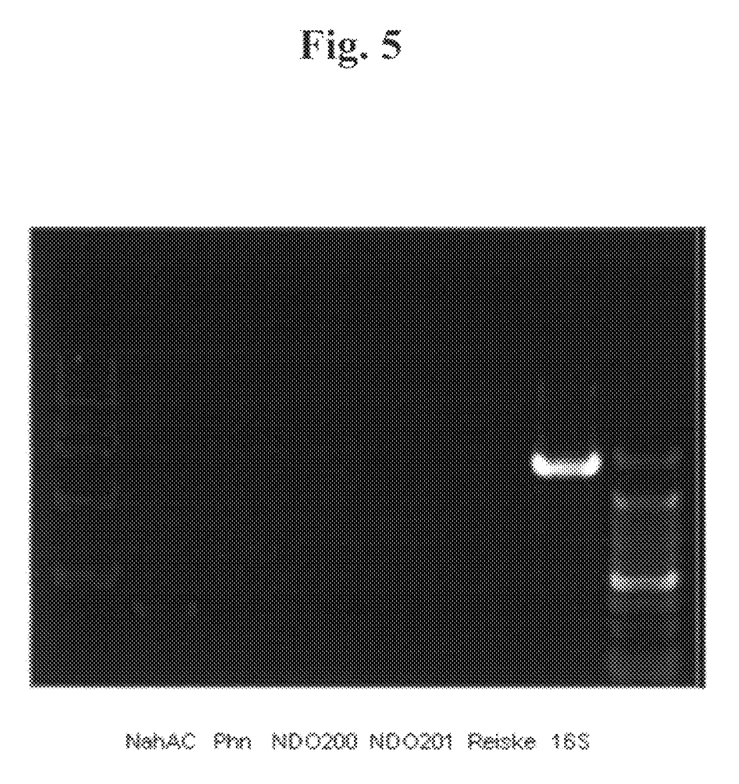
FIG. 5 represents PCR amplification using primers for detecting 16S rRNA partial gene of SN2 and well-known naphthalene-1,2-dioxygenase gene. Primer name and product size (bp) of each primer is nahAc 480 bp, NDO201 1.5 kb, NDO200 1.5 kb, Phn 993 by and Reiske 78 bp.

To detect dioxygenase gene, the SN2-type strain was subjected to PCR. As a result, no PCR products were detected, suggesting that SN2-type strain has novel type of naphthalene-1,2-dioxygenase gene, not known conventionally (FIG. 5).

8, Confirmation of Naphthalene Degradation Mechanism

According to conventional naphthalene degradation process, naphthalene is converted into 1,2-hydroxynaphthalene by naphthalene-1,2-dioxygenase. Indole could be detected as indigo color during oxidation by dioxygenase.

Figure 6:
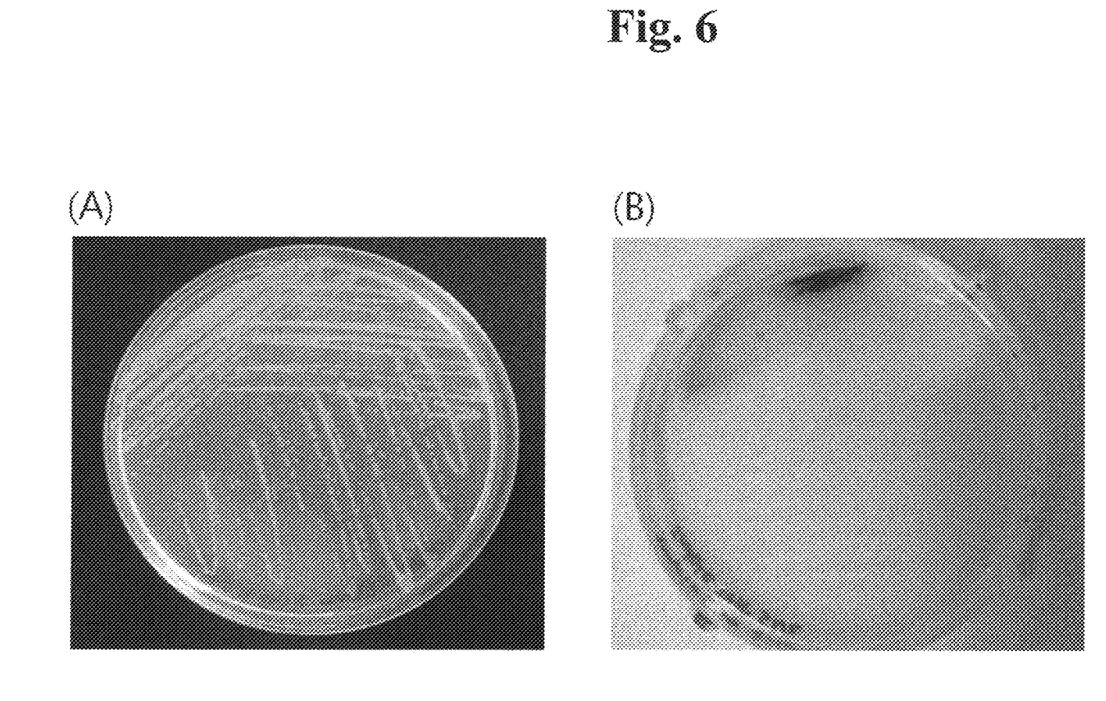
FIG. 6 represents results measuring a colorimetric reaction by indole to examine a metabolic pathway for degradation of ring compound (naphthalene and phenanthrene) in the SN2 strain selected. Panel (A) is a control group, and panel (B) is the SN2 strain group selected.

The media adjacent to the SN2 strain in media containing SN2 strain selected was observed as indigo color (FIG. 6). As a result, it could be appreciated that the SN2 strain is able to utilize naphthalene-1,2-dioxygenase in naphthalene degradation mechanism.

2. Discussion

In this study, it was demonstrated that naphthalene-degrading strains such as *Neptunomonas naphthovorans* sp., *Rhodococcus erythreus* sp. and *Pseudomonas* sp. were isolated from control and samples harvested in the offing of Taean-gun, and had no activity for degrading naphthalene. In addition, the SN2-type strain of *Alteromonas stellipolaris* sp. has been known to have no naphthalene-degrading activity, but showed a significant activity for degrading naphthalene. Consistently, the population analysis using DGGE verified that other species known to have an activity for degrading naphthalene conventionally show no degradation activity for naphthalene in a time-dependent manner, and only SN2-type strain is predominant species under naphthalene environment. Based on these results, it could be supposed that novel SN2-type strain species isolated from mudflats in the west coast have naphthalene-degrading activity.

More interestingly, it was demonstrated that the SN2-type strain has no conventional naphthalene-1,2-dioxygenase genes. Accordingly, it is suggested that the SN2-type strain may contain a naphthalene-1,2-dioxygenase gene having different nucleotide sequence, or degrade naphthalene using a novel mechanism unknown.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. ANDREW D. L, GARETH L. J, Quantification of phnAc and nahAc in Contaminated New Zealand Soils by Competitive PCR. *Appl. Environ. Microbiol;* 1814-1817 (2000). Ian M. H. D. Martin J, Wilfred F. M. R, Marine microorganisms make a meal of oil, *NATURE Reviews Microbiology;* 4:173 (2006).
2. ATSDR., Toxicological profile for polycyclic aromatic hydrocarbons (PAHs). Agency for Toxic Substances and Disease Registry, US Department of health and human services, US Public health service, Atlanta, Ga., p. 271 (1995).
3. BAIND, W. M. and S. L Ralston. carcinogenic polycyclic aromatic hydrocarbons (PAHs). *In comprehensive toxicology*, vol 12, Chemical (carcinogenic and anticarcinogens, ed. GTBowden and S>MDischer, 171-200. Amsterdam: Elsevier Press (1997).
4. GOAL, A. K and G. J Zylstra 1997. Genetics of naphthalene and phenanthren degradation by comamonas testosterone. *J. Odustrial Microbiol. Biotechnol;* 19: 401-407.
5. HARAYAMA, S., M, kok, and E. L. needle. Functional and evolutionary relation ships among diverse oxygenases. *Annu. Rev. Microbiol.* 46:565-601 (1992).
6. KESTER, D. R., DUEDALL, I. W., CONNOERS, D. N. and PYTKOWICZ, R. M. (1967). Preparation of Artificial Seawater. Limnology & Oceanography 12, 176-179.
7. MICHAEL J. L., CHRISTOPHER C. R. A, LEONID A. K, DAVID A. L, Purification and Characterization of a Novel Naphthalene dioxygenase from *Rhodococcus* sp. Strain NCIMB12038, *Appl. Environ. Microbiol.;* 181: 6200-6204 (1999).
8. STEFANIE Van T, TIHING-L T, JIFANG Y, JORIS M, Jean S, *Alteromonas stellipolaris* sp. nov., a novel, budding, prosthecate bacterium from Antarctic seas, and emended description of the genus *Alteromonas, Int J Syst Evol Microbiol;* 54:1157-1163 (2004).
9. STUCKER, I., J. BOUYER, L. Mandereau, and D. Hemon. 1993. Retrospective evaluation of the exposure to polycyclic aromatic hydrocarbons: comparative assessments with a job exposure matrix and by experts in industrial hygiene. *Int. J. Epidemiol.* 22:5106-5112.
10. YUKI K, HIDEO K, and Shigeaki H, Bacteria Belonging to the Genus Cycloclasticus Play a Primary Role in the Degradation of Aromatic Hydrocarbons Released in a Marine Environment, *Appl. Environ. Microbiol;* 68: 5625-5633 (2002).
11. Kester, D. R., Duedall, I. W., Connors, D. N. and Pytkowicz, R. M. (1967). Preparation of Artificial Seawater. *Limnology & Oceanography* 12, 176-179.
12. STUCKER, I., J. BOUYER, L. Mandereau, and D. Hemon., Retrospective evaluation of the exposure to polycyclic aromatic hydrocarbons: comparative assessments with a job exposure matrix and by experts in industrial hygiene, *Int. J. Epidemiol.* 22: 5106-5112 (1993).
13. Fetzer, J. C. The Chemistry and Analysis of the Large Polycyclic Aromatic Hydrocarbons. New York: Wiley (2000).

What is claimed is:

1. A biologically pure culture of a microbial strain, *Alteromonas* sp. SN2 as deposited with the Korean Collection for Type Cultures under Accession No. KCTC11700BP having an activity for degrading naphthalene and phenanthrene in contaminated soil, freshwater, and seawater samples.

2. A bioremediation process for naphthalene and phenanthrene contaminants, comprising contacting a microbial strain *Alteromonas* sp. SN2 as deposited with the Korean Collection for Type Cultures under Accession No. KCTC11700BP with naphthalene and/or phenanthrene contaminated soil, fresh water, or seawater.

3. A composition for purifying naphthalene and/or phenanthrene contaminated soil, fresh water, or seawater, comprising a biologically pure culture of microbial strain *Alteromonas* sp. SN2 as deposited with the Korean Collection for Type Cultures under Accession No. KCTC11700BP.

* * * * *